United States Patent
Das

(10) Patent No.: US 9,445,775 B2
(45) Date of Patent: Sep. 20, 2016

(54) SINGLE STEP DIFFERENTIAL PHASE CONTRAST X-RAY IMAGING

(71) Applicant: University of Houston System, Houston, TX (US)

(72) Inventor: Mini Das, Houston, TX (US)

(73) Assignee: UNIVERSITY OF HOUSTON SYSTEM, Houston, TX (US)

( * ) Notice: Subject to any disclaimer, the term of this patent is extended or adjusted under 35 U.S.C. 154(b) by 113 days.

(21) Appl. No.: 14/462,741

(22) Filed: Aug. 19, 2014

(65) Prior Publication Data
US 2015/0049860 A1 Feb. 19, 2015

Related U.S. Application Data

(60) Provisional application No. 61/867,218, filed on Aug. 19, 2013.

(51) Int. Cl.
*A61B 6/00* (2006.01)
*G01N 23/04* (2006.01)

(52) U.S. Cl.
CPC .............. *A61B 6/484* (2013.01); *A61B 6/4035* (2013.01); *A61B 6/4241* (2013.01); *A61B 6/482* (2013.01); *A61B 6/5205* (2013.01); *G01N 23/04* (2013.01); *G01N 2223/1016* (2013.01); *G01N 2223/423* (2013.01)

(58) Field of Classification Search
CPC ... A61B 6/484; A61B 6/4291; A61B 6/4035
See application file for complete search history.

(56) References Cited

U.S. PATENT DOCUMENTS

| | | | |
|---|---|---|---|
| 2009/0316857 A1* | 12/2009 | David | A61B 6/484 378/62 |
| 2016/0022235 A1* | 1/2016 | Ning | A61B 6/484 378/4 |

FOREIGN PATENT DOCUMENTS

WO 2013103408 A1 7/2013

OTHER PUBLICATIONS

Peter R.T. Munro et al., "Phase and Absorption Retrieval Using Incoherent X-ray Sources," PNAS, Aug. 28, 2012, vol. 109, No. 35, pp. 13922-13927.
Peter R.T. Munro et al., "A Quantitative, Non-Interferometric X-ray Phase Contrast Imaging Technique," Jan. 14, 2013, Optics Express, vol. 21, No. 1, pp. 647-661.
Allessandro Olivo et al., "A Coded-Aperture Technique Allowing X-ray Phase Contrast Imaging with Conventional Sources," Appl. Phys. Lett., Aug. 16, 2007, vol. 91, pp. 074106-1-3.
International Patent Application No. PCT/US2014/051602, International Search Report and Written Opinion dated Nov. 19, 2014, 9 pages.

* cited by examiner

*Primary Examiner* — Hoon Song
(74) *Attorney, Agent, or Firm* — Conley Rose, P.C.

(57) ABSTRACT

A system and method for single step and motionless x-ray phase contrast imaging. In one embodiment, a system for single step x-ray imaging includes a clinical x-ray source, a first coded aperture mask, a second coded aperture mask, and a photon counting spectral detector. The first coded aperture mask is disposed between the x-ray source and an object to be imaged. The photon counting spectral detector is disposed to detect x-rays passing through the object. The second coded aperture mask is disposed between the object to be imaged and the photon counting spectral detector. The system can provide, from a single acquisition step, an absorption image, a phase image, and differential phase image.

16 Claims, 2 Drawing Sheets

SINGLE STEP DIFFERENTIAL PHASE CONTRAST X-RAY IMAGING

CROSS-REFERENCE TO RELATED APPLICATIONS

This application claims the benefit of U.S. provisional patent application Ser. No. 61/867,218 filed Aug. 19, 2013, and entitled "Single Step Differential Phase Contrast X-Ray Imaging," which is hereby incorporated by reference in its entirety for all purposes.

BACKGROUND

The penetrative ability of x-rays makes them valuable for structural imaging applications ranging from medical imaging and materials research to quality control and security. Transmission imaging with x-rays is typically used to produce an attenuation contrast (AC) image of the material of interest. However, these images suffer from poor contrast sensitivity that poses severe limitations in many high-risk applications. The contrast sensitivity of transmission imaging is also an issue in medical imaging. Detection of early stage cancer (as represented, for example, by tumors smaller than 1 cm) is of vital importance. Transmission imaging is a workhorse imaging modality, yet is not sensitive enough to reliably detect such tumors.

SUMMARY

A system and method for generating absorption, phase, and differential phase images from a single x-ray exposure are disclosed herein. In one embodiment, a system for single step x-ray imaging includes a clinical x-ray source, a first coded aperture mask, a second coded aperture mask, and a photon counting spectral detector. The first coded aperture mask is disposed between the x-ray source and an object to be imaged. The photon counting spectral detector is disposed to detect x-rays passing through the object. The second coded aperture mask is disposed between the object to be imaged and the photon counting spectral detector.

In another embodiment, a method for single step x-ray imaging includes generating x-rays using a polychromatic x-ray source. The x-rays are filtered through a first coded aperture mask disposed between the x-ray source and an object to be imaged. The x-rays are further filtered through a second coded aperture mask disposed on a side of the object opposite the first aperture mask. The x-rays filtered through the second aperture mask are detected using a photon counting spectral detector. A differential phase contrast image of the object is generated based on output of the photon counting spectral detector.

In a further embodiment, a non-transitory computer-readable medium is encoded with instructions that when executed cause a processor to: activate a polychromatic x-ray source for generation of x-rays; to receive x-ray data from a photon counting spectral detector, the x-ray data comprising photon counts for x-rays filtered through a pair of coded aperture plates; and to process the x-ray data to generate a differential phase contrast image of an object disposed between the coded aperture plates.

BRIEF DESCRIPTION OF THE DRAWINGS

For a detailed description of exemplary embodiments of the invention, reference will now be made to the accompanying drawings in which.

NOTATION AND NOMENCLATURE

Figure 1:
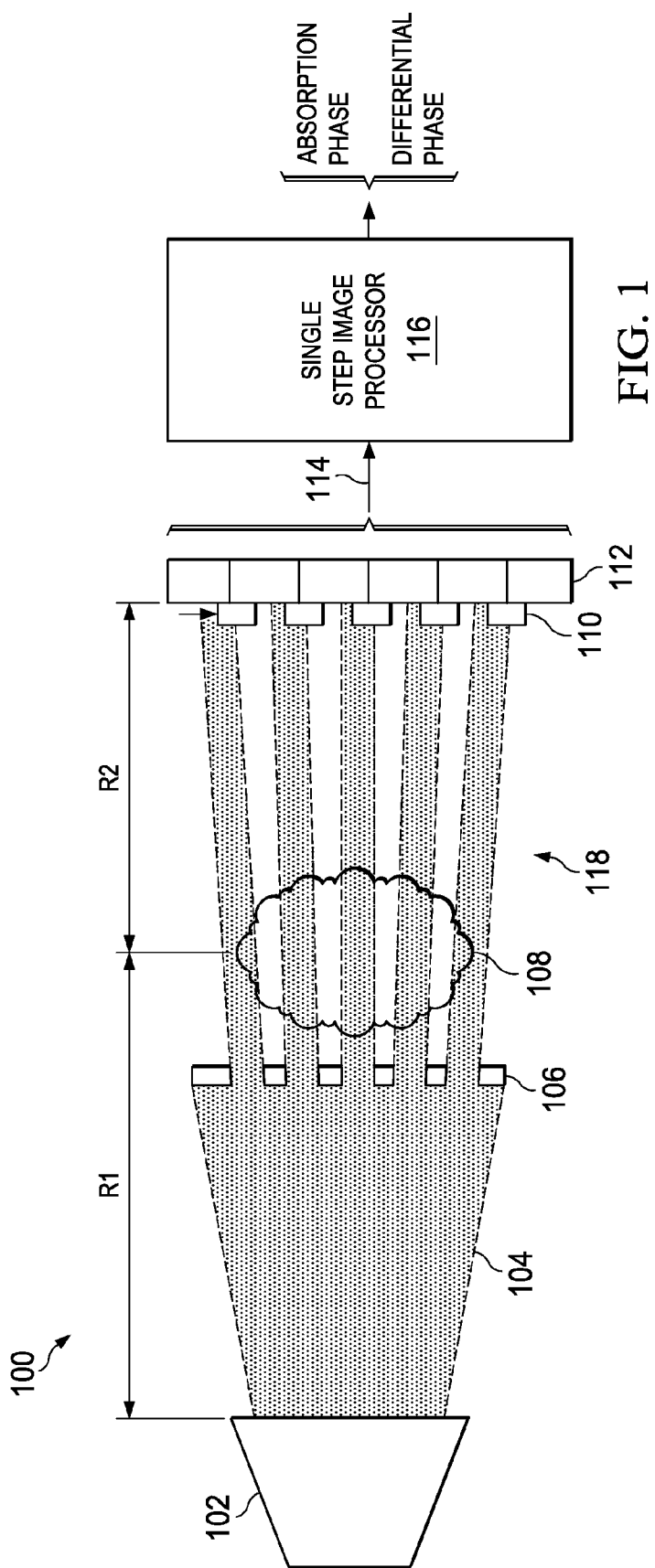
FIG. 1 shows a block diagram for a system for x-ray imaging that provides absorption, phase contrast, and differential phase contrast imaging in a single step in accordance with principles disclosed herein.

In the following discussion and in the claims, the terms "including" and "comprising" are used in an open-ended fashion, and thus should be interpreted to mean "including, but not limited to . . . . " In addition, the term "couple" or "couples" is intended to mean either an indirect or a direct connection. Thus, if a first device couples to a second device, that connection may be through a direct connection, or through an indirect connection accomplished via other devices and connections. Further, the term "software" includes any executable code capable of running on a processor, regardless of the media used to store the software. Thus, code stored in memory (e.g., non-volatile memory), and sometimes referred to as "embedded firmware," is included within the definition of software. The recitation "based on" is intended to mean "based at least in part on." Therefore, if X is based on Y, X may be based on Y and any number of other factors.

DETAILED DESCRIPTION

The following discussion is directed to various embodiments of the invention. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

The limited contrast sensitivity in attenuation contrast (AC) images is problematic in breast cancer screening and other x-ray applications. In digital mammography (DM) and digital breast tomosynthesis (DBT), radiologists must typically rely on structural artifacts and architectural distortions that appear in the images to diagnose malignant breast masses. For example, architectural distortion in the cancerous tissue is the only way to identify malignancy.

As electromagnetic waves, x-rays propagating through tissue or other material undergo phase change ϕ as well as attenuation. The magnitude of the phase change is determined by the real part of the tissue's complex refractive index:

$$n = 1 - \delta + \beta. \quad (1)$$

The imaginary part β is related to the linear absorption coefficient μ(E) through the equation:

$$\mu(E) = 4\pi\beta/\lambda. \quad (2)$$

The real part (δ) is:

$$\delta(E) = (\lambda^2 r_e \rho_e)/2\pi \quad (3)$$

where:
$r_e$ is the classical electron radius,
λ is the wavelength associated with energy E, and
$ρ_e$ is the electron density (ED) in the tissue.

If δ is a function of location (x, y, z), the phase change (retardation) is:

$$\phi(x, y; z, \lambda) = -\frac{2\pi}{\lambda} \int \delta(x, y, z'; \lambda) dz', \quad (4)$$

where the optic axis is assumed to be parallel to z. In accordance with equation (3), phase changes are directly linked to electron density variations in the tissue. With x-ray energies between 10 and 100 keV, phase changes in soft tissue may be 1000 times higher than attenuation changes.

Differential phase (DP) information (∇ϕ) is useful for depicting tissue boundaries, and phase sensitive imaging (PSI) methods that yield this information are broadly referred to as phase-contrast imaging (PCI) methods. Phase-contrast imaging may map the changes in phase, either by estimating ϕ directly or by estimating the gradient ∇ϕ or the Laplacian $\nabla^2\phi$ if there is insufficient contrast in ϕ alone.

Conventional techniques for x-ray phase imaging and/or differential phase imaging employ interferometric methods or coded aperture (CA) methods. These methods are problematic in that they require multiple measurements involving precise movement of the x-ray optics in multiple steps to provide x-ray absorption, phase contrast, and differential phase contrast (DPC) with quantitative accuracy. Interferometric methods require multiple stepping movements of x-ray gratings, and conventional coded aperture techniques require at least one dithering movement of the detector mask. The need for precise movement of the optics makes such methods unsuitable for clinical applications. Furthermore, the multiple measurements (i.e., multiple x-ray sessions or exposures) required by these techniques tend to increase the x-ray dosage applied to the imaged subject, which may be undesirable.

Embodiments of the present disclosure (systems and methods) provide retrieval of relevant properties of a material in a single step (single acquisition/session/exposure) rather than the multiple steps required by conventional methods. Additionally, the techniques disclosed herein do not require movement of optical components as is required in conventional systems. Accordingly, embodiments allow measurement of absorption, phase contrast, and differential phase contrast in a single step, thereby lowering the x-ray dose applied for imaging, and enabling phase sensitive imaging in clinical applications. Conventional x-ray systems, including conventional differential phase contrast imaging systems, are incapable of providing absorption, phase contrast, and differential phase contrast images from a single x-ray acquisition step.

Embodiments of the x-ray system disclosed herein are applicable to soft tissue imaging like breast imaging and prostate imaging, x-ray imaging of luggage in baggage claims, detection of explosives using x-ray imaging, object inspection, etc. Embodiments are also applicable to materials science and studies where an electron density map of thick objects is required, and embodiments may be applied in all phase retrieval methods using x-rays or other electromagnetic radiation.

FIG. 1 shows a block diagram for a system 100 for x-ray imaging that provides absorption, phase contrast, and differential phase contrast imaging in a single step in accordance with principles disclosed herein. The system 100 includes an x-ray source 102, an object mask 106, a detector mask 110, a photon counting spectral detector (PCSD) 112, and a single step imaging processor 116. The x-ray source 102 is a clinical x-ray source, such as an x-ray tube suitable for clinical use (e.g., a clinical x-ray tube). A clinical x-ray source may include an incoherent or polychromatic x-ray tube.

The object mask 106 is a coded aperture mask disposed between the x-ray source 102 and the object 108 being imaged. The object mask 106 creates, via the apertures therein, from the x-rays 104 emitted by the x-ray source 102, multiple single spatially coherent x-ray beams 118 (beamlets) that illuminate the object 108 being imaged. That is, the object mask 106 spatially filters the x-rays 104 by blocking a portion of the x-rays 104 to create the beamlets 118.

The detector mask 110 is a coded aperture mask disposed between the object 108 and the PCSD 112. The beamlets 118 pass through the object 108, where the amplitude and phase of the x-ray signals are affected by the composition of the object 108. After passing through the object 108, the beamlets 118 illuminate and are spatially filtered by the apertures of the detector mask 110. The object mask 106 and the detector mask 110 may include any of a variety of coded aperture patterns. In some embodiments of the system 100, coded aperture masks produced by Creatv MicroTech, Inc. may be suitable for use as the object mask 106 and/or the detector mask 110.

The PCSD 112 provides both temporal and energy discrimination of photons, for x-ray detection. Accordingly, the PCSD 112 provides single step measurement that simultaneously yields intensity measurements corresponding to photons of multiple energy levels. The system 100 may apply various photon counting x-ray detectors as the PCSD 112. Some embodiments apply Medipix (MED) detectors. Medipix detectors are photon-counting pixel detectors originally devised for astrophysical applications, and include a semiconductor sensor layer bonded to an electronics layer. The semiconductor layer is based on semiconductor material such as Si, CdTe, CdZTe and/or GaAs that generates an electron/hole cloud when radiation is incident thereon. The electronics count the number of events in each pixel (e.g., 256×256 pixels or more). The energy of each counted photon is compared to thresholds (which may be variably set) allowing for energy/wavelength discrimination. Some PCSDs can record the detection time and the energy of every detected photon (i.e., a timpix detector). Additionally, such detectors offer extremely low noise, high resolution (50 micron pixel size) and a large dynamic range.

The PCSD 112 separates detected photons into energy bins. With intensity measurements at two or more energies, embodiments of the system 100 can retrieve the absorption, phase contrast and differential phase contrast images from a single x-ray acquisition using analytic or numerical methods. Accordingly, using the PCSD 112 in conjunction with coded-aperture masks 106 and 110, embodiments of the system 100 can use intensity measurements obtained for at least two energies to simultaneously retrieve absorption (providing a map of effective atomic number of imaged object), phase (providing a map of object electron density) and differential phase (providing edge information). The intensity measurements using the coded aperture masks 106 and 110 are contributed to by object attenuation and differential phase changes (for a 1D mask, the differential phase will be in the direction of the coded aperture mask length) in the object which can be separated using a number of numerical or analytical methods when data is obtained at two or more energy bins. In some embodiments, a two-dimensional mask can be used to make measurements which can yield differential phase information in two directions in a single step.

The phase contrast imaging processor 116 is coupled to the PCSD 112. The x-ray image data 114, including amplitude, pixel event count, energy and/or time of detection of each photon, and which includes intensity measurements obtained for a plurality of energies, produced by the PCSD 112 is transferred to the single step image processor 116. The image processor 116 processes the x-ray image data to generate an attenuation (absorption) image, a phase contrast image, and/or a differential phase contrast image of the object 108 illuminated by the x-rays.

Figure 2:
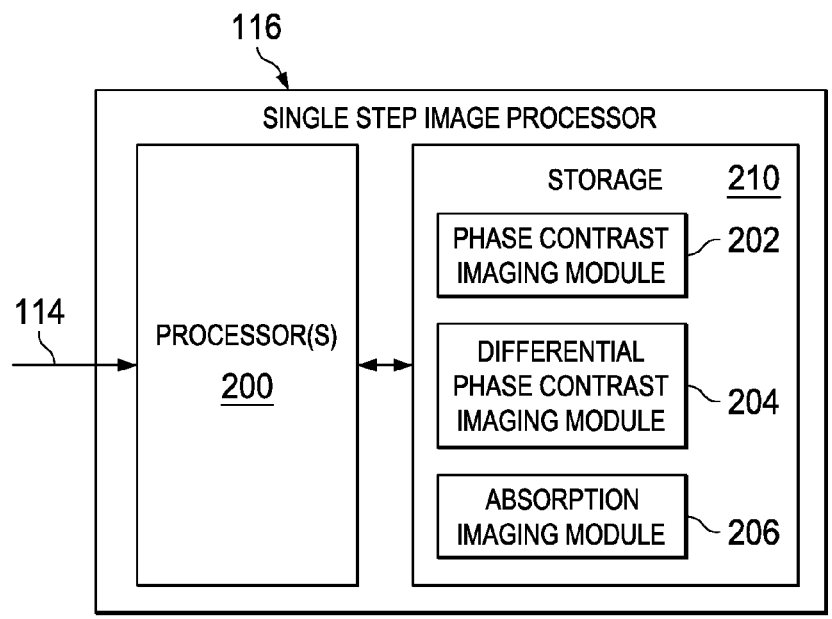
FIG. 2 shows a block diagram for an x-ray image processor for single step absorption, phase, and differential phase contract x-ray imaging in accordance with principles disclosed herein.

FIG. 2 shows a block diagram for the single step image processor 116 for single step x-ray absorption, phase contrast, and/or differential phase contrast imaging in accordance with various embodiments. The embodiment of the image processor 116 shown in FIG. 2 includes processor(s) 200 and storage 210 coupled to the processor(s) 200. The processor(s) 200 is an instruction execution device that executes instructions retrieved from the storage 210. Processors suitable for use as the processor(s) 200 may include general-purpose microprocessors, digital signal processors, microcontrollers, or other devices capable of executing instructions retrieved from a computer-readable storage medium. Processor architectures generally include execution units (e.g., fixed point, floating point, integer, etc.), storage (e.g., registers, memory, etc.), instruction decoding, peripherals (e.g., interrupt controllers, timers, direct memory access controllers, etc.), input/output systems (e.g., serial ports, parallel ports, etc.) and various other components and sub-systems.

The storage 210 is a non-transitory computer-readable storage medium suitable for storing instructions (e.g., software instructions) executable by the processor(s) 200. The storage 210 may include volatile storage such as random access memory, non-volatile storage (e.g., a hard drive, an optical storage device (e.g., CD or DVD), FLASH storage, read-only-memory), or combinations thereof. The storage 210 contains a phase contrast imaging module 202, a differential phase contrast imaging module 204, and an absorption imaging module 206. The phase contrast imaging module 202 includes instructions that when executed by the processor(s) 200 cause the processor(s) 200 to generate phase contrast images based on image data provided by the PCSD 112 as disclosed herein. Similarly, the differential phase contrast imaging module 204 includes instructions that when executed by the processor(s) 200 cause the processor(s) 200 to generate differential phase contrast images based on image data provided by the PCSD 112 as disclosed herein. The absorption imaging module 206 includes instructions that when executed by the processor(s) 200 cause the processor(s) 200 to generate absorption images based on image data provided by the PCSD 112.

The absorption, phase contrast, and differential phase contrast images respectively generated by the absorption imaging module 206, the phase contrast imaging module 202, and the differential phase contrast imaging module 204 may be produced from a single x-ray data set provided by the PCSD 112. The phase contrast imaging module 202, differential phase contrast imaging module 204, and absorption imaging module 206 cause the processor to generate corresponding phase, differential phase, and absorption images in accordance with the computations disclosed herein. Some embodiments of the image processor 116 may be implemented as a computer such as a desktop computer, a server computer, an array of computers, etc.

The single step image processor 116 utilizes spectral information provided by the PCSD 112 in conjunction with transport of intensity equation (TIE). The TIE relates changes in intensity distribution and phase variations as a function of propagation distance. For a monochromatic source with energy E, the intensity measured at the plane z=R can be modeled accurately as:

$$I(R, E) = I(0, E) - \frac{R}{k} I(0, E) \phi'(x) \tag{5}$$

where R is the propagation distance, $\phi'(x)$ is the derivative of phase in the x-direction (orthogonal to the direction of mask lines), and I(0,E) is the intensity at z=0 (the object plane). The single step image processor 116 can apply the TIE of equation (5) to describe differential phase contrast image formation due to edge illumination from the masks 106 and 110. While significantly simpler than conventional TIE implementations, the TIE of equation (5) distinctly separates the relative contributions of absorption, phase and differential phase changes in the measured x-ray intensity.

For a cone-beam geometry, embodiments adjust equation (5) to account for the magnification M:

$$I(R, E) = \frac{I(0, E)}{M^2}\left(1 - \frac{R}{Mk} \phi'(x)\right) \tag{6}$$

The intensity I(0,E) is related to the attenuation through the object, expressible as $$I(0, E) = I_f(0, E) \exp\left(-\int \mu(E) dz\right) \tag{7}$$

Here, $I_f$ is the flat-field intensity measured at the object plane and $\mu$ is the spatially varying and energy dependent linear attenuation coefficient of the object. By substituting equation (7) into equation (6) and making use of a Rytov approximation $$\frac{R}{Mk} \phi' \ll 1$$

that is suitable for weakly scattering objects, equation (8) is generated $$-\log\left(1 - \frac{M^2 I(R, E)}{I_f(E)}\right) = \int \mu(E) dz - \frac{R}{Mk} \phi'(x) \tag{8}$$

Equation (8) provides a starting point for deriving a phase-retrieval solution for CA-DPC imaging. Embodiments make use of a decomposition of the attenuation coefficient:

$$\mu(E) = NK \frac{z^4}{e^3(E)} + NZ\sigma_{KN}(E) \tag{9}$$

The right-hand terms of equation (9) correspond to the photoelectric (PE) and Compton scattering (CS) contributions to the attenuation of the object. In equation (9), N is the electron concentration, Z is the atomic number, e(E) is the normalized energy of the incident photon with respect to the energy of an electron, K is a dimensionless constant, and $\sigma_{K,N}$ is the scattering cross-section of an electron (computable from the Klein-Nishina equation).

The substitution of equations (5) and (9) into equation (8) produces $$-\log\left(\frac{M^2 I(R, E)}{I_f(E)}\right) = \frac{K}{e^3(E)}a_1 + \sigma_{KN}(E)a_2 + \frac{2\pi r_e R}{Mk^2(E)}a_3 \quad (10)$$

where $a_1$, $a_2$ and $a_3$ are energy independent constants related to the fundamental material properties of the object. These form the unknowns to be solved and they are defined as $$a_1 = \int \rho Z^4; \; a_2 = \int \rho dl; \; a_3 = \frac{da_2}{dx} = \frac{d\int \rho dl}{dx} \quad (11)$$

Solving for $a_1$ and applying the derivative can yield an unacceptably noisy estimate of $a_2$. Hence, $a_3$ is treated as an independent unknown, making three unknowns to be solved for. Obtaining signatures of differential phase imagery is an important advantage of the DPC imaging methods over PBPI (probe beam photo injection) where only photoelectric (PE) absorption and phase signatures are typically retrieved. Embodiments provide accurate solutions for all three parameters separately with quantitative accuracy. PE absorption, phase and differential phase relates to the energy independent material properties $a_1$, $a_2$ and $a_3$ respectively.

Equation (11) is valid for a wide range of x-ray energies and material properties and forms the underlying equation to solve for the object absorption, phase and differential phase image if multiple projection images are available for different energies or for different detector locations. Using the PCSD 112, embodiments simultaneously obtain projection data corresponding to multiple energies. However, even with data from multiple energy measurements, a unique solution of equation (11) is not possible due to the nonlinear energy dependence of $\mu$ for the energy range of interest (25-120 keV).

Embodiments of the PCSD 112 can separate the photons into B bins (b=1, . . . E), with $E_b$ being the corresponding median energy for bin b. The data thus acquired in the spectroscopic mode can also be summed to achieve data corresponding to a larger bin. In one example, counts from all or a plurality of bins are added to produce a single large bin with median energy $E_M$ corresponding to the entire spectrum being used for imaging. For data corresponding to each energy bin, equation 8 can be written as $$-\log\left(\frac{M^2 I(z = R, E_i)}{I_f(E_i)}\right) = \frac{K}{e^3(E_i)}a_1 + \sigma_{KN}(E_i)a_2 + \frac{2\pi r_e R}{Mk^2(E_i)}a_3 \quad (12)$$

The entire system of equations can be represented with the matrix-vector equation Ga=d, where a is a 3×1 solution vector, d is a B×1 data vector and G is a 3×B system matrix that contains energy dependent coefficients.

The image processor 116 may apply a least square solution type approach. The accuracy of the solution can be improved by increasing the number or energy bins. However, for a larger number of bins, due to decreasing photon counts per bin the benefit may not increase indefinitely. If bins are chosen with unequal number of counts (meaning equal spectral width but unequal counts for the different bins), the image processor 116 may employ a regularization strategy using a weighted least square approach.

The image processor 116 may apply various methods for obtaining the solutions from a projection measurement. A first method treats the problem as having three unknowns and uses data from 6 energy bins. The image processor 116 may use a weighted least square method applied in Fourier domain to obtain solutions of the form:

$$a = (G^T W G)^{-1} G^T W d \quad (13)$$

where W is a B×B diagonal weighting matrix containing the signal-to-noise ratio of the detected photons for each energy bin.

The values $a_1$, $a_2$, and $a_3$ based on equation (13) are energy independent and hence the absorption, phase and differential phase can be obtained for any desired energy by simple scalar multiplications. Knowing $a_1$, $a_2$, and $a_3$, the PE absorption $\mu_{PE}$ can be obtained from first term on the right hand side of equation (11), which is the same as $$K\frac{a_1}{e^3(E)}.$$

The phase ($\phi$) is obtained from equation (10) by substituting the obtained solution for $a_2$; the differential phase is $a_3$ (which is energy independent). The magnitude of $\mu_{PE}$ and $\phi$ changes with the x-ray energy.

While PCXDs offer the flexibility of choosing a number of bins, the Poisson noise corresponding to each data set increases when the total counts are divided into multiple bins. Some embodiments of the image processor 116 may apply a second method to solving for object absorption, phase and differential phase image that potentially provides improved fidelity. The data processed may be from six energy bins as per the first method. Equation (12) is rewritten to have only two unknowns:

$$-\log\left(\frac{M^2 I(z = R, E_i)}{I_f(E_i)}\right) = \frac{K}{e^3(E_i)}a_1 + \left(\sigma_{KN}(E_i) + \frac{2\pi r_e R}{Mk^2(E_i)}\nabla\right)a_2 \quad (14)$$

where definitions of $a_1$ and $a_2$ from equation (11) are still valid. The image processor 116 solves for $a_1$ and $a_2$ using weighted least squares as per the first method. Thereafter, embodiments consider a single large bin (generated, for example, by summing all the counts from various bins from the original data) with a median energy of $E_M$. Knowing $a_1$ and $a_2$, $a_3$ can be obtained from:

$$\frac{2\pi r_e R}{Mk^2(E_i)}a_3 = -\log\left(\frac{M^2 I(z = R, E_i)}{I_f(E_i)}\right)\frac{K}{e^3(E_i)}a_i - \sigma_{KN}(E_i)a_2 \quad (15)$$

In some implementations of the image processor 116, the second method described above, in which the absolute DPC is obtained in a two-step estimation algorithm using the data obtained from a single measurement, may exhibit better noise texture and lower RE than the first method described above.

Figure 3:
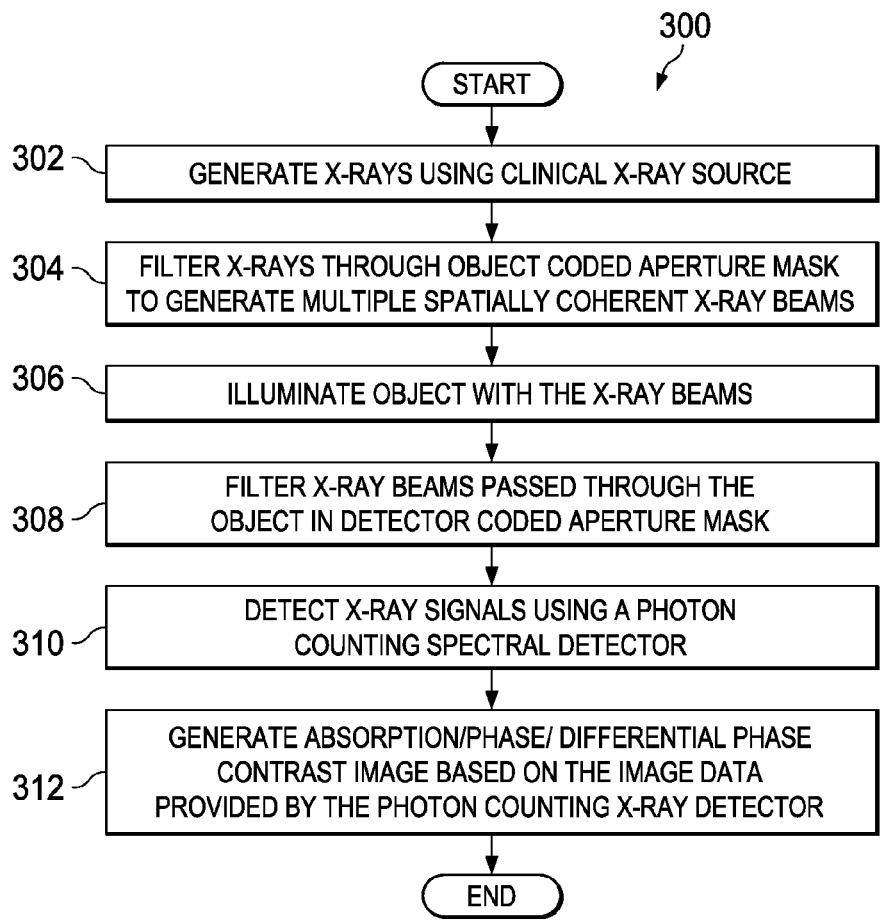
FIG. 3 shows a flow diagram for a method for single step absorption, phase, and differential phase contract x-ray imaging in accordance with principles disclosed herein.

FIG. 3 shows a flow diagram for a method for single step absorption, phase, and differential phase contract x-ray imaging in accordance with principles disclosed herein. Though depicted sequentially as a matter of convenience, at least some of the actions shown can be performed in a different order and/or performed in parallel. Additionally, some embodiments may perform only some of the actions shown. In some embodiments, at least some of the operations of the method 300, as well as other operations described herein, can be implemented as instructions stored in computer readable medium 210 and executed by the processor(s) 200.

In block 302, the x-ray source 102 generates an x-ray beam 104. The x-ray source 102 may be a clinical x-ray tube. The processor(s) 200 may control the x-ray source 102.

In block 304, the x-rays generated by the x-ray source 102 pass through an object coded aperture mask disposed between the x-ray source 102 and the object to be imaged (e.g., object 108). The apertures of the coded aperture mask filter the x-rays into a plurality of spatially coherent x-ray beamlets 118.

In block 306, the plurality of spatially coherent x-ray beamlets 118 illuminate the object 108. The object 108 may attenuate and/or change the phase of the x-ray signals as the beams 118 pass through the object 108.

In block 308, the beamlets 118, having passed through the object 108, are filtered through the apertures of the detector coded aperture mask 110.

In block 310, the x-ray beamlets passing through the apertures of the detector coded aperture mask 110 are detected by the PCSD 112. For each photon detected by the PCSD 112, the time of detection, energy level, and per pixel count may be determined and recorded. Thus, the PCSD 112 provides intensity measurements corresponding to photons of multiple energy levels.

In block 312, the PCSD 112 provides the x-ray data, including amplitude, energy level, detection time, count per pixel, etc. to the single step image processor 116. The image processor 116 processes the x-ray data 114 provided by the PCSD 112 to generate an absorption image, a phase contrast image, and/or a differential phase contrast image of the object 108 based on a single x-ray illumination of the object 108. The x-ray data processing provided by the image processor 116 may be in accordance with the computations described above.

Additionally, some embodiments may collect phase sensitive intensity measurements of the object 108 from various projection angles, and produce from the multiple measurements tomographic images of absorption, phase, and differential phase for the object 108. For example, x-ray tube 102, masks 106 and 110, and detector 112 may be rotated about the object 108 to acquire multiple phase sensitive intensity measurements, and the measurements processed as disclosed herein to yield a complete tomographic image of electron density, effective atomic number, and gradient of electron density in the object 108.

The above discussion is meant to be illustrative of the principles and various embodiments of the present invention. Numerous variations and modifications will become apparent to those skilled in the art once the above disclosure is fully appreciated. For example, while embodiments have been described with regard to a photon counting x-ray detector, those skilled in the art will understand that embodiments may employ other spectral detectors. It is intended that the following claims be interpreted to embrace all such variations and modifications.

What is claimed is:

1. A system for single step x-ray imaging, comprising:
   a clinical x-ray source;
   a first coded aperture mask disposed between the x-ray source and an object to be imaged;
   a photon counting spectral detector disposed to detect x-rays passing through the object;
   a second coded aperture mask disposed between the object to be imaged and the photon counting spectral detector; and
   an image processing system configured to generate a differential phase contrast image of the object based on output of the photon counting spectral detector;
   wherein the image processor is configured to model the intensity of the x-rays at the photon counting spectral detector as:

$$I(R, E) = I(0, E) - \frac{R}{k} I(0, E) \phi'(x).$$

2. The system of claim 1, wherein the image processing system is configured to generate the differential phase contrast image based on output of the x-ray source generated in a single session.

3. The system of claim 1, wherein the imaging processor is configured to generate an absorption image, a phase contrast image, and a differential phase contrast image based on data acquired by the photon counting spectral detector during a single x-ray illumination of the object.

4. The system of claim 1, wherein the imaging processor is configured to provide an image based on spectrally dependent attenuation derived from data acquired by the photon counting spectral detector during a single x-ray illumination of the object.

5. The system of claim 1, wherein the image processor is configured to:
   estimate values for a plurality of different energy independent properties of the object, each of the properties corresponding to one of object absorption, phase and differential phase image; and
   estimate object absorption, phase and differential phase image images based on the properties.

6. The system of claim 5, wherein the image processor is configured to:
   estimate the value of the energy independent property corresponding to the differential phase contrast image based on the values of the energy independent properties corresponding to the object absorption and phase images.

7. A method for single step x-ray imaging, comprising:
   generating x-rays using a polychromatic x-ray source;
   filtering the x-rays through a first coded aperture mask disposed between the x-ray source and an object to be imaged;
   filtering the x-rays through a second coded aperture mask disposed on a side of the object opposite the first aperture mask;
   detecting the x-rays filtered through the second aperture mask using a photon counting spectral detector;

modeling the intensity of the x-rays at the photon counting spectral detector as:

$$I(R, E) = I(0, E) - \frac{R}{k}I(0, E)\phi'(x);$$

and
generating a differential phase contrast image of the object based on output of the photon counting spectral detector.

8. The method of claim 7, further comprising generating the differential phase contrast image based on output of the x-ray source generated in a single session.

9. The method of claim 7, further comprising generating an absorption image, a phase contrast image, and a differential phase contrast image based on data acquired by the photon counting spectral detector during a single x-ray illumination of the object.

10. The method of claim 7, further comprising generating an image based on spectrally dependent attenuation derived from data acquired by the photon counting spectral detector during a single x-ray illumination of the object.

11. The method of claim 7, further comprising
estimating values for a plurality of different energy independent properties of the object, each of the properties corresponding to one of object absorption, phase and differential phase image;
estimating object absorption, phase and differential phase image images based on the properties; and
estimating the value of the energy independent property corresponding to the differential phase contrast image based on the values of the energy independent properties corresponding to the object absorption and phase images.

12. The method of claim 7, further comprising:
acquiring a plurality of x-ray measurements with the photon counting spectral detector, each of the measurements corresponding to x-rays passing through the object at a different angle;
generating tomographic images of absorption, phase, and differential phase of the object based on the plurality of measurements.

13. A non-transitory computer-readable medium encoded with instructions that when executed cause a processor to:
activate a polychromatic x-ray source for generation of x-rays;
receive x-ray data from a photon counting spectral detector, the x-ray data comprising photon counts for x-rays filtered through a pair of coded aperture plates;
model the intensity of the x-rays at the photon counting spectral detector as:

$$I(R, E) = I(0, E) - \frac{R}{k}I(0, E)\phi'(x);$$

and
process the x-ray data to generate a differential phase contrast image of an object disposed between the coded aperture plates.

14. The computer-readable medium of claim 13 encoded with instructions that when executed cause the processor to generate the differential phase contrast image based on output of the x-ray source generated in a single session.

15. The computer-readable medium of claim 13 encoded with instructions that when executed cause the processor to generate an absorption image, a phase contrast image, and a differential phase contrast image based on a data acquired by the photon counting spectral detector during a single x-ray illumination of the object.

16. The computer-readable medium of claim 13 encoded with instructions that when executed cause the processor to provide an image based on spectrally dependent attenuation derived from data acquired by the photon counting spectral detector during a single x-ray illumination of the object.

* * * * *